US008352045B2

(12) United States Patent
Joucla et al.

(10) Patent No.: US 8,352,045 B2
(45) Date of Patent: Jan. 8, 2013

(54) DEVICE FOR STIMULATING LIVING TISSUE BY MICROELECTRODES AND REMOVABLE MODULE AND USE THEREOF (75) Inventors: Sébastien Joucla, Le Bouscat (FR); Blaise Yvert, Carignan de Bordeaux (FR); Lionel Rousseau, Le Perreux sur Marne (FR)

(73) Assignees: Centre National de la Recherche Scientifique (CNRS), Paris (FR); Group Ecole Superieure d'Ingenieurs en Electronique et Electrotechnique, Noisy-le-Grand (FR); Universite de Bordeaux 1, Talence (FR)

( * ) Notice: Subject to any disclaimer, the term of this patent is extended or adjusted under 35 U.S.C. 154(b) by 467 days.

(21) Appl. No.: 12/739,069

(22) PCT Filed: Oct. 20, 2008

(86) PCT No.: PCT/EP2008/064133
§ 371 (c)(1),
(2), (4) Date: Apr. 21, 2010

(87) PCT Pub. No.: WO2009/053333
PCT Pub. Date: Apr. 30, 2009

(65) Prior Publication Data
US 2011/0208029 A1    Aug. 25, 2011

(30) Foreign Application Priority Data
Oct. 22, 2007    (FR) ...................................... 07 07369

(51) Int. Cl.
*A61N 1/08*    (2006.01)
*A61N 1/18*    (2006.01)

(52) U.S. Cl. .......................... 607/116; 607/152; 600/373
(58) Field of Classification Search .................. 607/116, 607/152; 600/373
See application file for complete search history.

(56) References Cited

U.S. PATENT DOCUMENTS
4,969,468 A    11/1990    Byers et al.
(Continued)

FOREIGN PATENT DOCUMENTS
EP    1723983 A    11/2006
(Continued)

OTHER PUBLICATIONS
Borkholder, D. A. et al.: "Microelectrode arrays for stimulation of neural slice preparations," Journal of Neuroscience Methods 77 (1997) p. 61-66.
(Continued)

*Primary Examiner* — Carl H Layno
*Assistant Examiner* — Natasha Patel
(74) *Attorney, Agent, or Firm* — Harness, Dickey & Pierce, P.L.C.

(57) ABSTRACT

The disclosure relates to a device for stimulating living tissue, comprising an array of stimulating microelectrodes that are placed in a defined configuration side by side and able to be selected by applying an electrical signal for stimulation by one of the microelectrodes. According to the disclosure, an additional conducting surface for application against the living tissue, is provided in the vicinity of a defined plurality of sections for local application of microelectrodes, connecting structures being provided for electrical connection between the zones, and the additional conducting surface being also connected to a lead and being formed so as to ensure local stimulation via a microelectrode.

30 Claims, 7 Drawing Sheets

U.S. PATENT DOCUMENTS

| | | | |
|---|---|---|---|
| 5,411,540 | A | 5/1995 | Edell et al. |
| 5,938,689 | A | 8/1999 | Fischell et al. |
| 6,032,062 | A | 2/2000 | Nisch |
| 6,132,683 | A | 10/2000 | Sugihara et al. |
| 6,151,519 | A | 11/2000 | Sugihara et al. |
| 6,297,025 | B1 | 10/2001 | Sugihara et al. |
| 6,324,429 | B1 | 11/2001 | Shire et al. |
| RE38,323 | E | 11/2003 | Sugihara et al. |
| 7,006,859 | B1 | 2/2006 | Osorio et al. |
| 7,632,674 | B2 * | 12/2009 | Xing et al. ............ 435/287.3 |
| 7,937,153 | B2 * | 5/2011 | Zhou et al. .................. 607/54 |
| 2004/0267344 | A1 | 12/2004 | Stett et al. |
| 2005/0203366 | A1 | 9/2005 | Donoghue et al. |
| 2006/0135862 | A1 | 6/2006 | Tootle et al. |
| 2006/0265039 | A1 | 11/2006 | Bartic et al. |
| 2007/0067007 | A1 * | 3/2007 | Schulman et al. ......... 607/115 |
| 2007/0142863 | A1 | 6/2007 | Bradley |
| 2007/0179584 | A1 * | 8/2007 | Gliner ...................... 607/152 |
| 2010/0023102 | A1 * | 1/2010 | Spruit ....................... 607/116 |
| 2011/0230747 | A1 * | 9/2011 | Rogers et al. .............. 600/377 |

FOREIGN PATENT DOCUMENTS

| | | |
|---|---|---|
| WO | 2005/087309 A | 9/2005 |

OTHER PUBLICATIONS

Cunningham, W. et al.: "Fabrication of microelectrode arrays for neural measurements from retinal tissue," Journal of Physics D: Applied Physics 34 (2001) 2804-2809.

Fromherz, P.: "Sheet conductor model of brain slices for stimulation and recording with planar electronci contacts," Eur. Biophys. J. (2002) 31: 228-231.

McIntyre, C.C. et al.: "Finite Element Analysis of the Current-Density and Electric Field Generated by Metal Microelectrodes," Annals of Biomedical Engineering, vol. 29, pp. 227-234, 2001.

Wagenaar, D. A. et al.: "Effective parameters for stimulation of dissociated cultures using multi-electrode arrays," Journal of Neuroscience Methods 138 (2004) 27-37.

Grumet, A. E. et al.: "Multi-electrode stimulation and recording in the isolated retina," Journal of Neuroscience Methods 101 (2000) 31-42.

Heuschkel, M. O. et al.: "A three-dimensional multi-electrode array for multi-site stimulation and recording in acute brain slices," Journal of Neuroscience Methods 114 (2002) 135-148.

English translation of International Preliminary Report on Patentability, IB, Geneva, established Jun. 1, 2010.

* cited by examiner

DEVICE FOR STIMULATING LIVING TISSUE BY MICROELECTRODES AND REMOVABLE MODULE AND USE THEREOF

CROSS-REFERENCE TO RELATED APPLICATIONS

This application is a National Phase Entry of International Application No. PCT/EP2008/064133, filed on Oct. 20, 2008, which claims priority to French Application 07/07369, filed on Oct. 22, 2007, both of which are incorporated by reference herein.

BACKGROUND AND SUMMARY

The invention concerns a device to stimulate living tissue with an array of microelectrodes.

Arrays of microelectrodes are used in neurophysiological or pharmacological applications for example. These arrays are used to record the electrical activity of a living tissue (cell or multicell activities). They are also used to stimulate a tissue electrically. This applies to any type of excitable tissue, notably nerve tissue, muscle e.g. cardiac tissue, or stem cells.

It is notably sought to be able to achieve focal stimulation of a nerve tissue. One long term application concerns neuroprostheses and targets the development of microstimulators to be implanted in the body (notably the human body but also in animal), to generate electric stimulations and compensate for the ill-functioning of neuron networks in the event of disease or anomaly of a body organ. The stimulations may for example be deep stimulations of the brain for neurodegenerative diseases (e.g. Parkinson's, Alzheimer, dementia), of the spinal cord in the event of motor disorders, or for the treatment of pain e.g. muscle pain or of sensory structures such as the peripheral nerves, retina, cochlea (inner ear) or other sensory relays.

To be able to stimulate living neurons, the array of microelectrodes must therefore be sized to the scale of the living tissue to be stimulated. Stimulation microelectrodes usually have a diameter in the order of a few tens of micrometres or less, and are spaced by a few hundred micrometres or less. However, for more macroscopic stimulation of the central or peripheral nervous system, larger electrodes (of mm or cm order) are used.

Documents [1] to [6] cited below, describe arrays of stimulation electrodes and methods for their use. The array may comprise several tens or even several hundred stimulation microelectrodes. Document [1] for example provides for an array with 36 stimulation microelectrodes and 4 reference electrodes. Document [5] makes provision for dividing the microelectrodes into two groups, one used for stimulation, the other used for recording, thereby doubling the number of microelectrodes.

One of the problems encountered with microelectrodes is to obtain focal stimulation of the living tissue. In an array of stimulation microelectrodes, if a stimulation signal is sent to one of the microelectrodes, it is to stimulate the region of the nerve tissue located facing this microelectrode.

Figure 1:
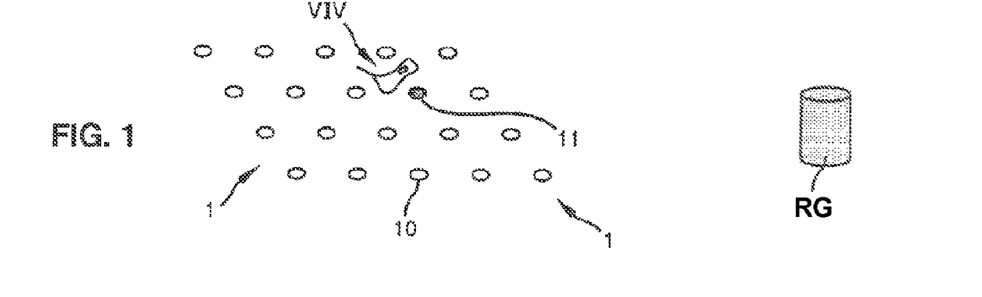
FIGS. 1 and 2 are schematic perspective views of known examples of microelectrode arrays.
Figure 2:
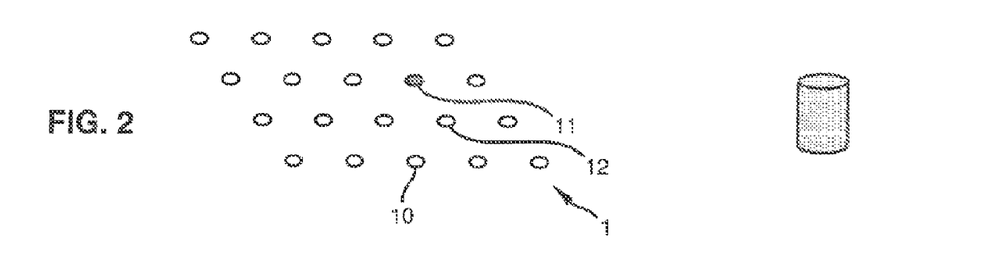

Monopolar stimulations are known in which the stimulation of a living cell VIV is made between a stimulation microelectrode 11 from among the stimulation microelectrodes 10 of the array 1 and a remote ground RG of the array 1 of stimulation microelectrodes, as is illustrated in FIG. 1. With bipolar stimulation, as illustrated in FIG. 2, stimulation is made between two stimulation microelectrodes 11 and 12 of the array 1. These two types of stimulation are not fully satisfactory however, insofar as with monopolar stimulation, an electrode distant from a neuron can nevertheless activate this neuron with the same current as an electrode close to this neuron, and with bipolar stimulation, there is a blind spot where neurons close to the stimulating electrodes are not excited.

Document [8] WO 2005/087309 describes an arrangement of electrodes for the excitation of nerves or muscles, which consists of replacing large-size electrodes by a group of electrodes of smaller size occupying an overall space that is comparable to the space occupied by the large electrode. These groups form a single stimulation site. Each stimulation site comprises three or five groups each consisting of electrically conductive surface elements which are connected together via conductor lines. An array of electrodes comprises seven stimulation sites each having five groups each consisting of electrically conductive surface elements connected together via conductor lines. The use of groups of electrodes for each stimulation site allows more homogeneous potential distribution in the stimulated region opposite the stimulation site than obtained with a single, large-size electrode. This leads to homogenization of stimulations which is detrimental to their focusing.

Document [7] provides a method for preferential stimulation of neural somas, whereby a stimulation electrode is positioned in the vicinity of the region of neural tissue, the electrode comprising a first inner conductive region that is disk-shaped surrounded by a second conductive region that is ring-shaped, the first and second conductive regions being separated by an insulating region. The stimulation current is delivered between the central circular conductor and the ring conductor, this ring conductor providing a current return loop. The lateral dispersion of current in the neural tissue is contained within a more local region than with monopolar stimulation, which means that the number of somas activated by the electrode is limited, solely including those close to the central electrode. This device has the twofold disadvantage that the connections of the stimulation electrode need to be doubled, and higher currents need to be delivered in order to stimulate the local cells.

The invention sets out to overcome these disadvantages with an array of stimulation microelectrodes arranged in a determined side-by-side configuration and able to be selected for application of an electric stimulation signal by one of the microelectrodes. In particular, it must be possible for the stimulation device to be generalized to a large number of stimulation microelectrodes in the array, whilst being easy to implement.

For this purpose, the subject of the invention is a device to stimulate living tissue, comprising an array of microelectrodes arranged in a determined side-by-side configuration and selectable for application of an electric stimulation signal by one of the microelectrodes, the microelectrodes being insulated from each other and each comprising a conductor to send a stimulation signal, having a section for local application to the living tissue, characterized in that, in addition to the microelectrode conductors, it comprises at least one supplemental conductive surface for application in whole or in part against the living tissue, this surface being insulated from the microelectrode conductors and comprising a plurality of conductive zones respectively located in the vicinity of a determined plurality of sections for local application of microelectrodes of the array, connection means being provided to ensure electric connection between the conductive zones of the supplemental surface, the supplemental conductive surface also being connected to at least one port intended to be connected to an external conductor returning at least part of the stimulation signal and being formed to ensure focal stimulation from at least one of the determined plurality of microelectrodes.

According to embodiments of the invention:

The supplemental conductive surface is integrated in the same support as that of the microelectrodes, Or the supplemental conductive surface is integrated on a different support to that of the microelectrodes.

The supplemental conductive surface is in the form of a grid whose conductive zones are formed by meshes passing around microelectrodes, the connection means being formed on the supplemental surface by the intersections between meshes.

Said meshes passing around microelectrodes each surround a single microelectrode.

The grid is formed by rectilinear secant lines.

Each of the meshes of the grid surrounding a microelectrode forms a stimulation pixel restricted to the space delimited by this mesh.

The supplemental conductive surface passes between microelectrodes.

The supplemental conductive surface surrounds microelectrodes.

The supplemental conductive surface is continuous with openings for passage of the local application sections of microelectrodes.

The supplemental conductive surface comprises electrically parallel branches between microelectrodes and each passing in the vicinity of several microelectrodes.

The electric connection means between the different conductive zones are located at least in part in the supplemental conductive surface.

The electric connection means are located at least in part outside the supplemental conductive surface, inside or outside a support of the supplemental conductive surface or in a supplemental external electric circuit.

The supplemental conductive surface has interface surface electric conductivity (interface conductivity between the electrode and the tissue) of 100 S/m$^2$ or higher at a frequency of 100 Hz to 1,000 Hz.

The supplemental conductive surface has interface surface electric conductivity (interface conductivity between the electrode and the tissue) of 1,000 S/m$^2$ or higher at a frequency of 100 Hz to 1,000 Hz, and preferably 40,000 S/m$^2$ or higher at a frequency of 100 Hz to 1,000 Hz.

The array of microelectrodes has a spacing pitch between microelectrodes, and said conductive zones of the supplemental surface pass at a distance from the plurality of microelectrodes that is equal to or less than five times the maximum spacing pitch between micro electrodes, and preferably at a distance equal to or less than the minimum spacing pitch between microelectrodes.

Said conductive zones of the supplemental surface pass at a distance from the plurality of microelectrodes that is equal to or less than 500 μm.

The device comprises a multiplicity of electric ports for access to the microelectrodes, which are respectively associated with the multiplicity of microelectrodes of the array, the port of the supplemental conductive surface 3 being single and separate from the electric ports of the microelectrodes.

The device comprises a multiplicity of electric ports for access to the microelectrodes, which are respectively associated with the multiplicity of microelectrodes of the array, the port of the supplemental conductive surface being multiple and separate from the electric ports of the microelectrodes.

The device comprises a multiplicity of electric ports for access to the microelectrodes, which are respectively associated with the multiplicity of microelectrodes of the array, the port of the supplemental conductive surface being single and separate from the electric ports of the microelectrodes, for each supplemental conductive surface if there is a plurality thereof.

The microelectrodes located on the edge of the array delimit a region for application against the living tissue, and the edge or port of the supplemental conductive surface is located outside the application region of the microelectrodes.

The device further comprises a first system to generate electric stimuli or stimulation currents and to deliver these to the tissue via the microelectrodes, and also to amplify and multiplex the signals recorded with the microelectrodes. This system is connected to the microelectrodes and to the surface port. The device also comprises a second system for acquisition and control provided with a man-machine interface to control the first system for the purposes of sending to at least one preselected microelectrode a predetermined stimulation signal on the man-machine interface, and to collect the activity of the living tissue responding or not responding to the stimulation signal for its reproduction on the man-machine interface.

The microelectrodes located on the edge of the array delimit a region for application against the living tissue, and the surface port is located inside the application region of the microelectrodes.

The device is implemented in contact with a living tissue, or part of a living organ, in vivo or in vitro, a cell preparation, an explant, a living organism, a laboratory system, an isolated living organ, part of an isolated living organ, or an implant for a living being.

A second subject of the invention is a removable assembly intended to be mounted in the device such as described above characterized in that, on one same removable module or distributed over several separate removable modules, it comprises the array of microelectrodes, said supplemental surface, an input-output electric interface circuit for electric connection of the microelectrodes and of the supplemental surface with the outside, comprising a multiplicity of electric terminals for access respectively to the multiplicity of microelectrodes of the array and a terminal for access to the supplemental surface separate from the electric terminals of the microelectrodes. A third subject of the invention is use of the device such as described above for the recording of signals emitted by a living tissue.

BRIEF DESCRIPTION OF THE DRAWINGS

The invention will be better understood on reading the following description given solely as a non-limiting example with reference to the appended drawings in which.

DETAILED DESCRIPTION

Extracellular electric stimulation of a living tissue consists of causing an electric current to pass through a combination of electrodes placed in contact with the tissue. Some electrodes inject a positive current in the tissue, whereas others simultaneously inject a negative current into the tissue, so that the sum of the amplitudes of the positive currents is equal to the sum of the amplitudes of the negative currents. To inject these currents, potential values are applied to the electrodes. These values are determined relative to a ground electrode which by definition has a potential of 0 V.

The simplest stimulation is monopolar stimulation. This consists of injecting a current (positive or negative) into a single electrode: a potential is applied to a single electrode. Therefore, the current is returned via the ground which is at potential 0 V. Conventionally, the ground is positioned at a large distance from the stimulation electrodes, generally of mm order.

To obtain spatially more focal stimulations, multipolar stimulations are conventionally used: not one but several electrodes are used in combination to which different potentials are applied (hence the term multipolar). For example, bipolar stimulation is used by applying different potential values to 2 electrodes generally positioned side by side, so that in general the currents passing through the two electrodes are of identical amplitude and of opposite sign. Similarly tripolar stimulation uses 3 electrodes, in general so that the current injected by one central electrode returns in equal parts via the two others surrounding it. In multipolar configurations, if the levels of potential applied to the different electrodes do not allow the positive and negative currents to offset one another fully, a residual current will return via the ground electrode.

During multipolar stimulation, several electrodes brought to different potentials are used in combination. However, despite the plurality of electrodes involved, this group of electrodes forms a single stimulation unit. The use of arrays of electrodes allows arrays to be constructed containing several stimulation units. The simplest case is the case with monopolar stimulations in which each electrode of the array (together with the ground) forms a unit. In this case, there are as many units as there are electrodes. To focus the stimulations, each stimulation unit can consist of several electrodes. For example, it is possible to create bipolar units consisting of pairs of electrodes, but this approach has the drawback however of having to double the number of microelectrodes of the array to obtain the same number of stimulation units.

One of the advantages of the invention is to provide a number of stimulation units equal to the number of electrodes in the array, whilst obtaining a gain in stimulation focusing. Another advantage is that loss of stimulation amplitude is small.

In FIGS. 3 to 10, each microelectrode 11 of the array 1 comprises an application conductor 21 intended to be applied against a living tissue and capable of acting as stimulation microelectrode to send it a stimulation signal. The stimulation current therefore passes in this conductor 21. This conductor is insulated from the conductors of the other electrodes, and is partly insulated from the living tissue. Each microelectrode conductor 21 comprises a section 210 for local application to the living tissue, which is its part facing the living tissue and necessarily touching it, for example formed by the tip of the conductor 21 and being circular for example. Each microelectrode conductor 21 also comprises an external port 13 that is generally individual, allowing the connection of an electric circuit to the support 40 of the array 1. The spacing pitch between the microelectrodes 11 can be set at a determined value for the entire array, or it may have different values for different regions of the array. The ports 13 are generally insulated from each other at the support of the array.

One or more supplemental conductive surfaces 3 are arranged in the vicinity of some or all the microelectrodes 11. Each surface 3 and the microelectrodes 11 are positioned so that they can jointly be applied against the living tissue, and the surface 3 is used to return the stimulation current sent by an adjacent microelectrode by focusing it in the vicinity thereof. The sections 210 and the surface 3 generally face the same side vis-à-vis the tissue. The ports 13 for access to the stimulation microelectrodes 11, the conductors 21 and the sections 210 are electrically insulated from the surface 3, for example by passing in layers different from the one of the surface 3 above or below this surface. The conductive sections 210 and the conductive surface 3 are exposed on the side of application against or in the living tissue.

The surface 3 therefore comprises conductive zones 31 located in the vicinity of some application sections 210 of microelectrodes, these zones being connected together so that they are substantially equipotential. The surface 3 is used as means for focusing in common several application sections 210 of different microelectrodes 11. According to the invention, the grid or supplemental surface 3 is not at the same potential as the stimulating microelectrodes 11, which is not the case in document [8] WO 2005/087309 in which the purpose is to homogenize stimulation and hence the potential is the same on all the microelectrodes of the same stimulation site.

Each microelectrode 11 generally forms a single stimulation site. However, several microelectrodes can be selected simultaneously for stimulation, which corresponds to the simultaneous use of several stimulation sites. Each local application section 210 generally forms a single stimulation site. The supplemental surface 3 or grid, via its port 33, 35, is set at an electric potential that is generally different from the potential sent to the microelectrodes 11 via their port 13, for example for stimulation via the application section 210 of the microelectrode 11 that has been selected. The potential of the supplemental surface 3 is generally set at zero Volts, but can be set at a value different to zero Volts. The supplemental surface can ensure the full or partial return of the stimulation current delivered by the microelectrodes 11 selected for stimulation. In general, a single supplemental surface 3 is provided in common for all the microelectrodes 11. Several supplemental surfaces 3 can be used individually or jointly preferably at the same potential. There may also be several supplemental surfaces 3 brought to different potentials e.g. of at least 0.1 millivolt (0.1 mV). The potential of the at least one supplemental surface 3 is different from the potential of at least one microelectrode 11 of said determined plurality of microelectrodes 11, for example of at least 0.1 millivolt (0.1 mV).

The number of supplemental surfaces used is preferably less than one tenth of the number of microelectrodes 11 in the array which can be selected for stimulation in the area of application under consideration. In the embodiment shown in FIG. 3, the supplemental surface is formed of a conductive grid 3 inserted between the microelectrodes 11 whilst surrounding the microelectrodes. The grid 3 comprises meshes 31 forming the conductive zones surrounding the microelectrodes 11, these zones 31 being connected conductively to each other via nodes and branches 32 of the grid 3. The grid 3 comprises meshes 31 arranged in the space located between adjacent microelectrodes 11.

In the embodiment shown in FIGS. 3, 4, 5, 6 and 7, each mesh 31 or opening 36 surrounds a single associated microelectrode 11. Each mesh can however surround a plurality of microelectrodes. Each stimulation microelectrode 11 and its associated conductor 21 are electrically insulated from the surface 3.

In the embodiments shown in FIGS. 3, 4, 5, 6 and 8, the surface 3 only requires a single external conductor 35 for return of the stimulation signal sent by one of the stimulation microelectrodes 11 to the living tissue, and a single access terminal 33 to connect the surface 3 to the external return conductor 35. Therefore, there is no need to insert an supplemental access conductor between the stimulation microelectrodes 11 for return of the stimulation signal. The array of stimulation microelectrodes 11 provided with surface 3 and their ports 13 and 33 can be arranged in a removable independent module 1 which, in its input-output electric circuit 16 for interface with the outside, has the electric ports 13 for access to the microelectrodes 11 and the terminal 33 for access to the surface 3. This independent module 1 can be mounted on a base 4 respectively having terminals 41 for electric connection to the ports 13 of the stimulation microelectrodes 11, and the terminal 35 for electric connection to port 33. This module 1 may also itself contain all or part of the recording and stimulation electronics, notably for implants.

This provides both focal and spatially homogeneous stimulation of the living tissue around the stimulating microelectrode 11. The problem of focusing stimulations is solved in very simple technological manner using a single counter-electrode formed by the surface 3 ensuring return of the current, even if several microelectrodes 11 stimulate simultaneously. The invention allows the introduction of the notion of a stimulation pixel restricted to each stimulation microelectrode 11, which may be of capital importance when constructing retina implants in which each region of the retina must be stimulated locally in a manner that is non-correlated with the other regions. In addition, the invention dispenses with multipolar stimulations which require multiplication of the number of stimulating electrodes and necessitate more current to activate the cells, creating non-homogeneous stimulation zones.

Figure 3:
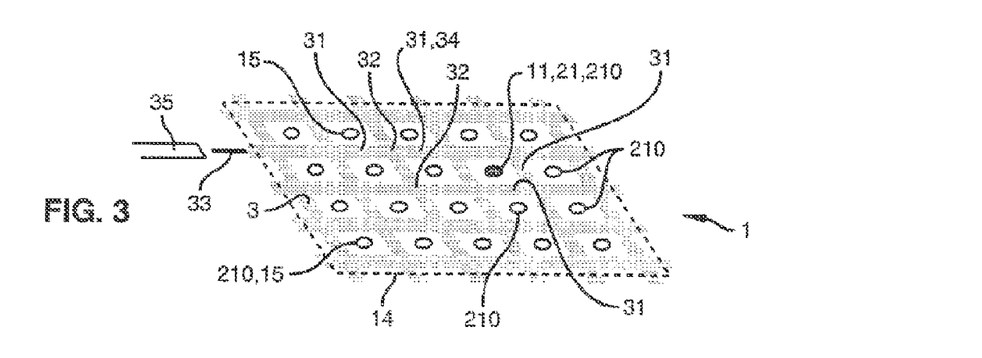
FIGS. 3, 5, 6, 7, 8, 9 are schematic perspective views of first, second, third, fourth, fifth and sixth embodiments of an array of stimulation microelectrodes according to the invention.
Figure 4:
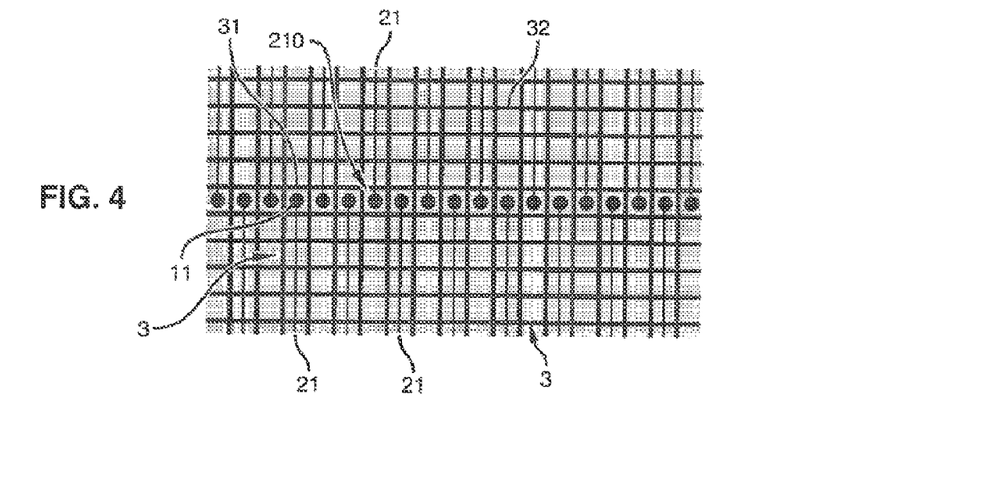
FIG. 4 shows an example of embodiment of a linear array of stimulation microelectrodes according to the invention.

For example, the microelectrodes 11 have a regular arrangement, such as orthogonal rows and columns in FIG. 3, the grid 3 then possibly being formed of orthogonal straight lines passing through the spaces between the stimulation microelectrodes 11. Evidently, the microelectrodes 11 and grid 3 could have any other arrangement.

The stimulation microelectrodes 11 are distributed in a region 14 for application of the stimulation device against the living tissue, this application region 14 for application being delimited by the stimulating microelectrodes 15 positioned on the edge of the array 1. The port 33 for access to the surface 3 generally lies outside the application region 14 of the microelectrodes 11, without passing between the stimulation microelectrodes 11, contrary to the prior art devices described above. However, a direct access to the surface 3 can be envisaged out of the plane of the microelectrodes 11, for example through the thickness of the support of the microelectrodes.

Evidently, a remote ground, distant from the stimulation microelectrodes 11 and the surface 3, can be provided in addition to the surface 3 for the return of the stimulation current. However, if the conductivity of the remote ground is greater than the conductivity of the surface 3, stimulation may be less focussed than without the remote ground.

The application sections 210 of the stimulation microelectrodes 11 and the surface 3 can be in any form e.g. planar but also curved. The surface 3 may optionally be inserted on a support different from the support of the microelectrodes 11 e.g. for in vivo 3D applications. In the embodiment shown in FIG. 4, the surface 3 is in the form of a grid according to FIG. 3, with application sections 210 of stimulation microelectrodes 11 aligned in a horizontal line, each section 210 being surrounded by a mesh 31, the grid 3 possibly having other meshes 32 not surrounding any microelectrode.

Figure 5:
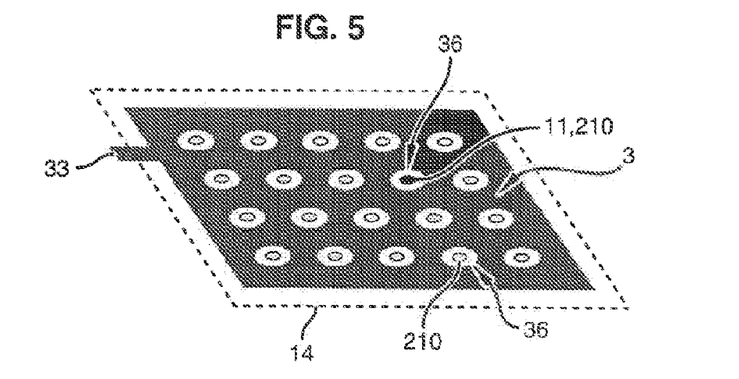

In the embodiment shown in FIG. 5, the supplemental conductive surface 3 is continuous in region 14 with openings 36 for passing of sections 210 of the microelectrodes 11, separated by a determined distance from the latter and for example of matching shape. In the embodiments illustrated in FIGS. 6 and 7, the conductive zones 31 in the vicinity of sections 210 each surround a section 210 at a distance from the section. The shape of the conductive zones 31 for example matches the shape of the sections 210 e.g. ring-shaped for circular sections 210.

Figure 6:
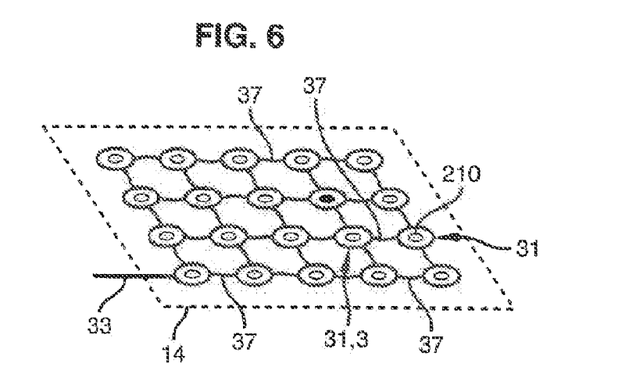
Figure 7:
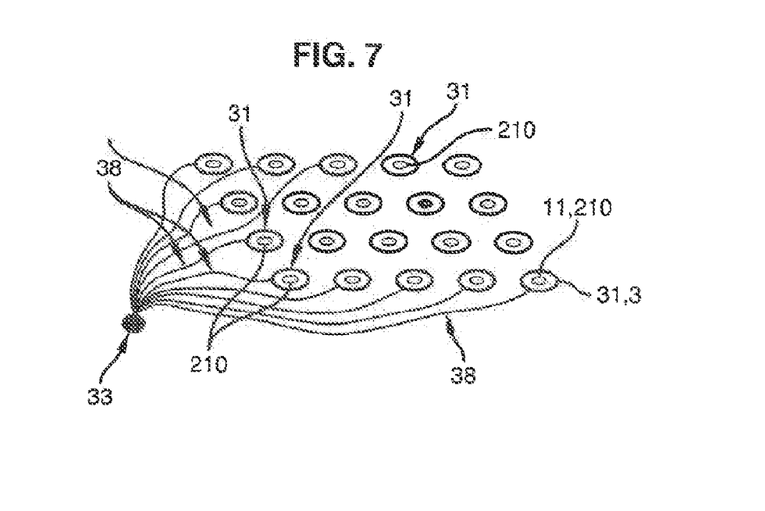

In the embodiment illustrated in FIG. 6, the zones 31 in the vicinity of the sections 210 are connected to each other via lugs 37 that are also conductive, for example in two secant directions in region 14, these lugs 37 forming part of the surface 3 and may or may not be applied against the living tissue and may or may not be straight. In the embodiment shown in FIG. 7, the zones 31 in the vicinity of the sections 210 are connected to each other via conductors 38 outside the surface 3 and are not applied against the living tissue when the array 1 and the surface 3 are applied. The external conductors 38 are connected to the port 33.

Figure 8:
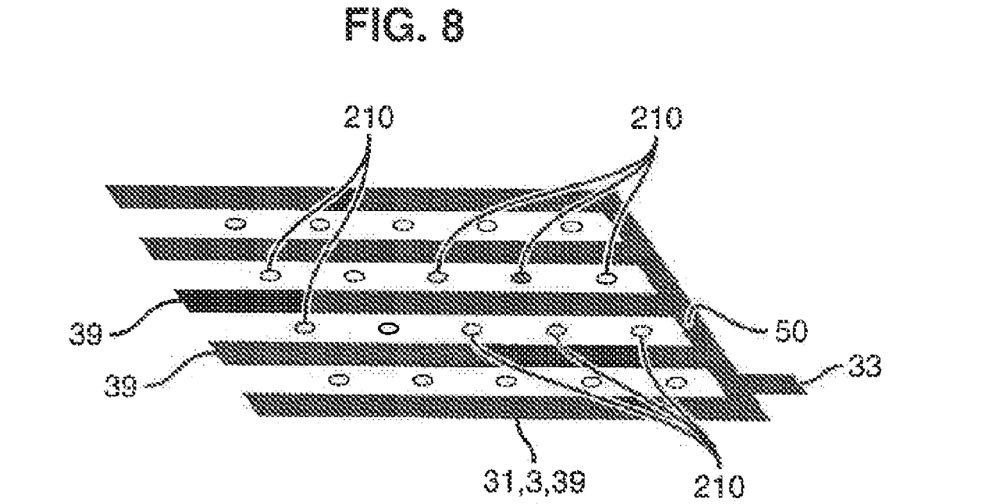
Figure 9:
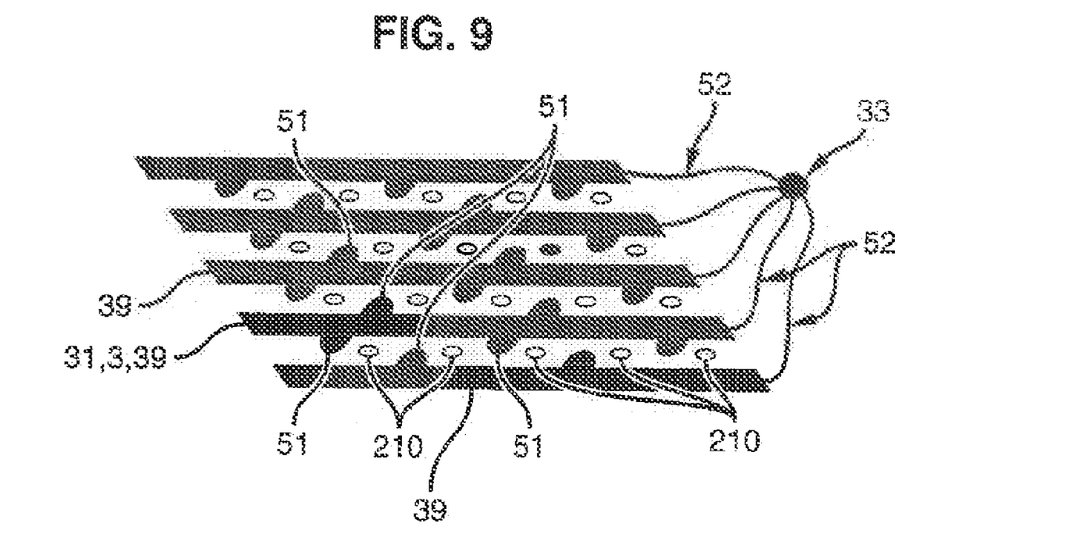

In the embodiments shown in FIGS. 8 and 9, the zones 31 in the vicinity of the sections 210 comprise branches 39 extending between sections 210 following a determined continuous pathway passing close to several successive sections 210 positioned on the same side, for example between several rows of sections 210. The branches 39 are electrically parallel being connected to each other, for example via a cross-member 50, this cross-member 50 being part of the surface 3 to be applied against the living tissue and may or may not be rectilinear, and/or connection means 52 similar to the conductors 38 can be provided. The branches 39 are rectilinear for example and physically parallel to one another.

In the embodiment illustrated in FIG. 9, at least one of the branches 39 supplementally comprises cross extensions 51 between two successive sections 210 situated on the same side of the branch 39. These extensions 51 alternate for example along the branch 39. In the illustrated example, if several branches 39 are provided, the extensions 51 of one branch do not touch the other branches 39 and also alternate from one branch 39 to the adjacent branch. Evidently, the indications given above for the surface 3 can be provided for all (as illustrated) or for a sub-assembly of microelectrodes 11 of the array 1.

Figure 10:
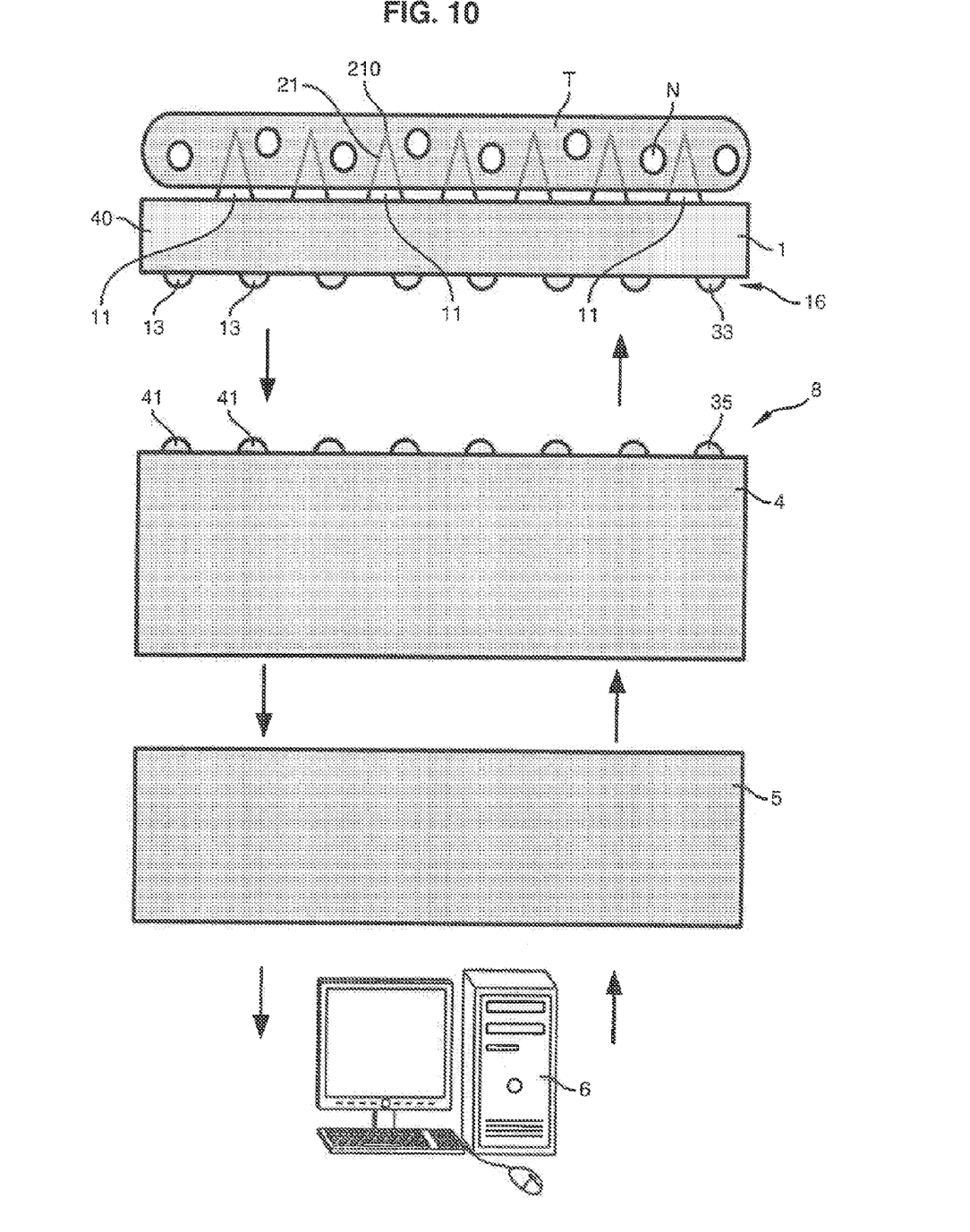
FIG. 10 shows an electronic measuring and stimulation system which can be used with the array of microelectrodes according to the invention.

In FIG. 10 the stimulation device 8 comprises a system 4 to generate stimuli, formed for example of an application-specific integrated circuit (ASIC) connected firstly to the terminals 13 for access to the microelectrodes 11 of the array 1 and to the terminal 33 for access to the surface 3, and secondly to a system 5 for acquisition, stimulation and control provided with a man-machine interface 6 consisting of a computer for example. The array 1, via its region 14 which comprises the sections 210 of stimulation microelectrodes 11 and the surface 3, is applied in vitro against the living tissue T having neurons N. Via system 4 under the control of system 5, stimulation signals are sent to the array 1 which were predetermined by interface 6, as illustrated by the vertical upward arrows in FIG. 7. The array 1 may also record the activity of the living tissue T responding or not to the stimulation signals, this activity being transmitted to the system 4 then to system 5 to be reproduced on interface 6 as illustrated by the vertical downward arrows in FIG. 7. Evidently, the array 1 of microelectrodes according to the invention could also act as reference electrode to measure variations in potential in a living tissue reflecting the electric activities of excitable cells forming this tissue. The array may also be applied to a tissue in vivo notably for functional rehabilitation (auditory, visual, neurodegenerative or cardiac diseases for example) or to investigate the central nervous system or other types of systems (fundamental research).

Figure 11:
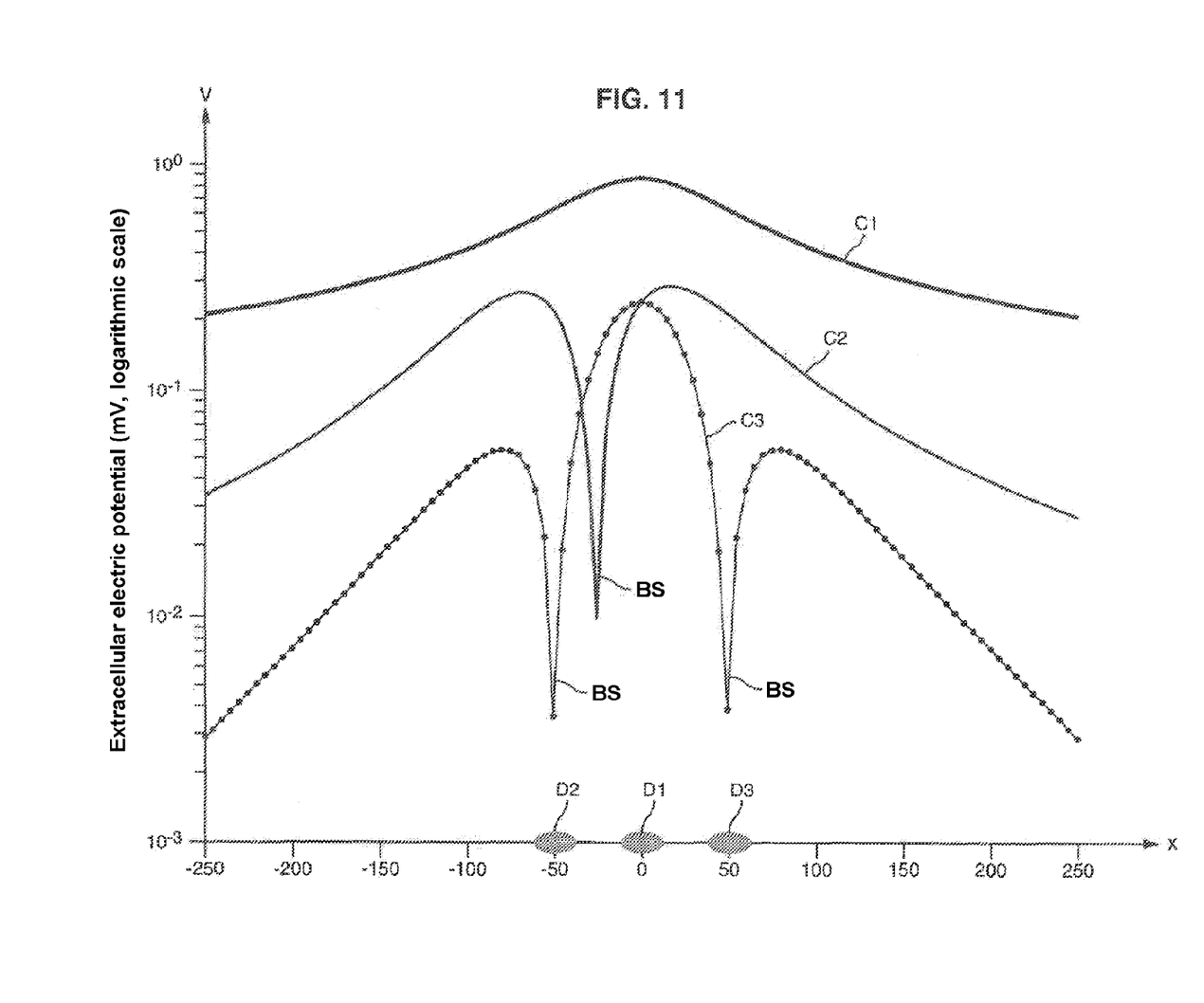
FIG. 11 is a diagram showing the electric potential in relation to the distance from a stimulating microelectrode for different types of stimulation.
Figure 12:
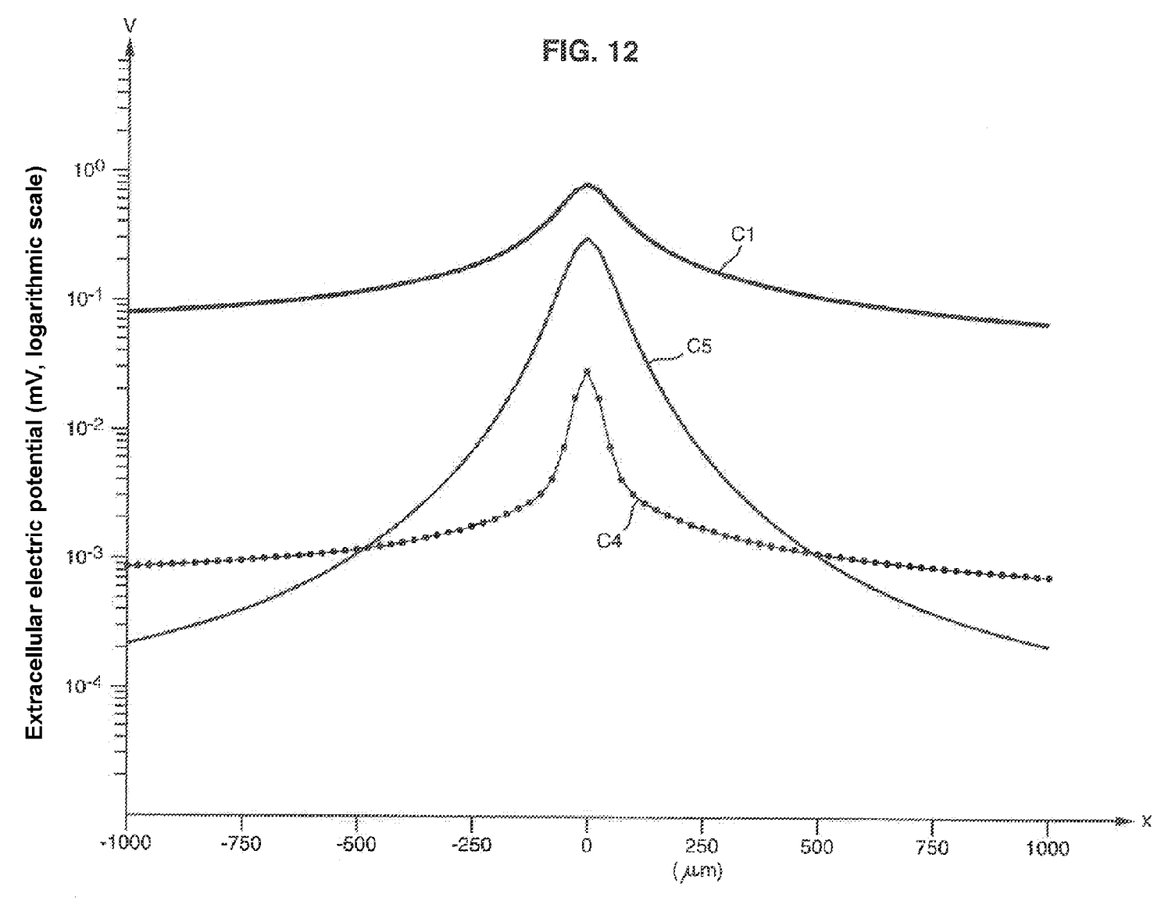
FIG. 12 is a diagram showing the electric potential in relation to the distance from a stimulating microelectrode for different types of configuration.
Figure 13:
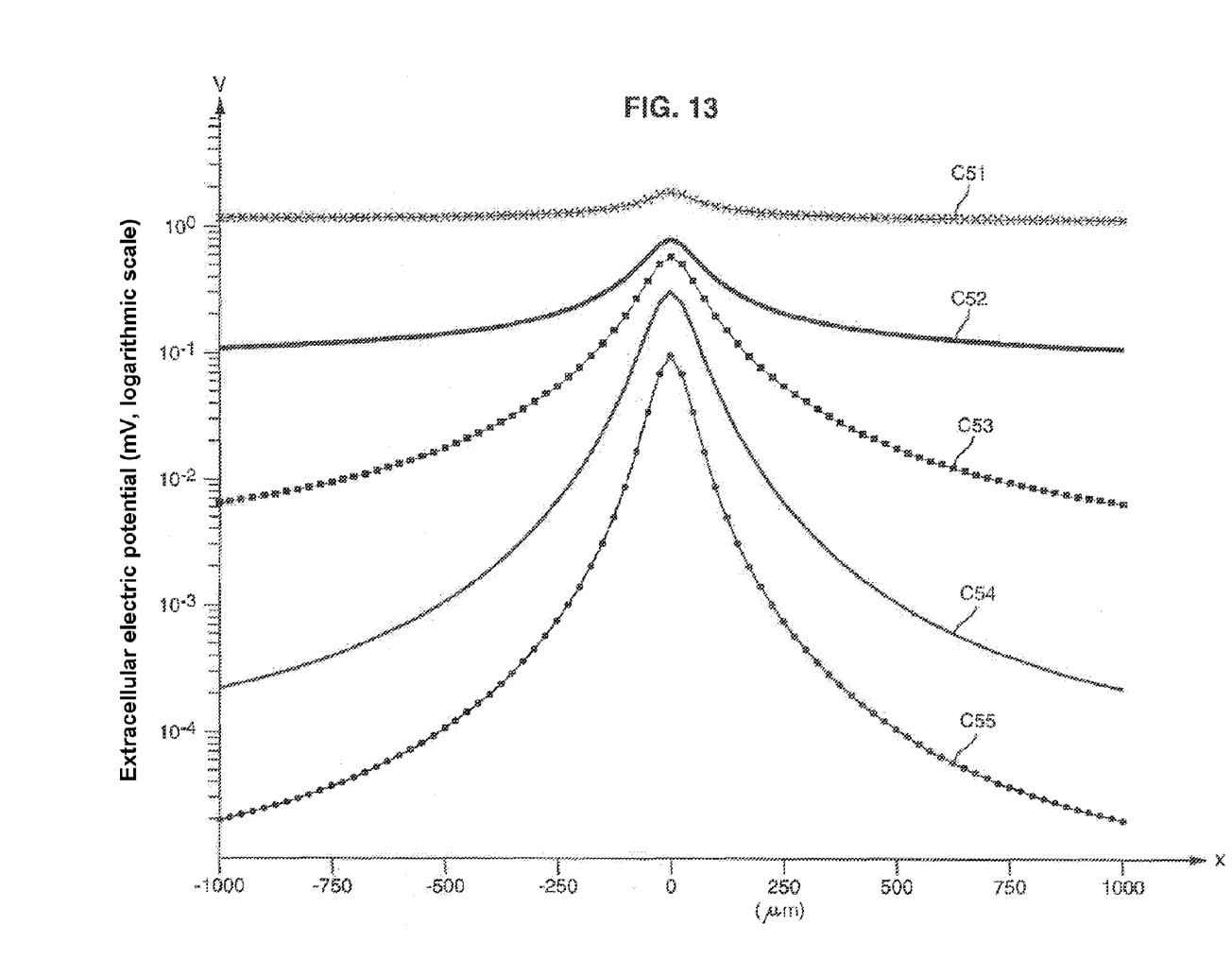
FIG. 13 is a diagram showing the electric potential in relation to the distance from a stimulating microelectrode for different surface conductivities.

The focusing of an extracellular stimulation is directly related to the steepness of the field potential around the stimulation electrode; the steeper this field (i.e. grows quickly with distance) the more current is needed to stimulate at large distance. Therefore, focusing stimulation amounts to focusing the field potential around the stimulation electrode. FIGS. 11, 12, 13 show the progression of field potential for different configurations of electrodes.

FIG. 11 shows the progression of the potential V (in absolute value) on a line passing 50 microns above the electrodes, for monopolar (curve C1), bipolar (curve C2) and tripolar (curve C3) stimulations. Monopolar stimulation consists of causing the current to pass between an electrode and a remote ground, bipolar stimulation consists of causing the current to pass between two adjacent electrodes, and tripolar stimulation consists of injecting a current into an electrode and causing half of the current to return in two electrodes located either side. In FIG. 11, the three grey disks D1, D2, D3 indicate the positions at 0 μm, −50 μm and +50 μm of the electrodes aligned along axis x of the abscissa for tripolar stimulation. For monopolar stimulation, only the central electrode D1 is used. For bipolar stimulation, the two left electrodes D1 and D2 are used. With monopolarity, the progression C1 of the potential is scarcely steep and hence scarcely focal. With bipolarity, the curve C2 is steeper but has a zone close to the electrodes where the potential is very low (blind spot ZA). Similarly, with tripolarity, the curve C3 is even steeper, but this time two blind spots ZA can be seen close to the electrodes. Therefore, multipolar configurations are more focal but the field is not homogeneous around the electrodes and notably has blind spots where the cells, which are nevertheless close to the electrodes, will not be stimulated.

In one embodiment of the invention, a grid is used (or a plane=filled grid, more generally called a surface) which passes around all the electrodes of the array and ensures the return of all or part of the stimulation current, irrespective of which electrode is used for stimulation. The potential of this surface is preferably maintained at ground potential, but this is not a necessity. FIG. 12 shows the progression of the potential V for 3 types of configurations in relation to the distance x along the abscissa from a stimulating microelectrode positioned at x=0 μm:
   curve C1 in the first monopolar configuration of FIG. 11,
   curve C4 in a second configuration according to patent U.S. Pat. No. 5,411,540 in which a single electrode is provided, formed by an inner conductive disk 10 microns in diameter surrounded by a conductive ring of outer diameter of 25 microns and radial width of 3 microns centred on the disk,
   curve C5 in a third configuration of the present invention with a surface 3 as in FIG. 5 whose openings 36 have a diameter of 25 microns, and the central electrodes 11 are disks of diameter of 10 microns centred on these openings.

The potential obtained by curve C5 is continuous and monotonic in relation to the distance from the stimulating microelectrode. In the second configuration, when the ring is at the same potential as a remote ground, the field potential is identical to that of C1 generated in the monopolar configuration and the focusing of stimulation is not improved. In the second configuration according to curve C4, when the ring ensures the complete return of the current without any current returning via a remote ground, stimulation is more focal than with monopolar stimulation but for one same delivered current the electric potential is much lower and hence less efficient. The present invention with a ground grid according to curve C5 gives highly focal stimulation and a potential amplitude very close to the amplitude obtained with monopolarity in the vicinity of the stimulation electrode. In addition, for a distance of more than 200 microns, the ground grid better focuses the potential than the ring in the second configuration: the attenuation of curve C5 is greater than that of curve C4. This solution therefore has three advantages compared with the second configuration: 1) no doubling of the number of electrodes, 2) less current needed for an amplitude identical to the potential close to the electrode, which is of importance having regard to the fact that it is difficult to design small-size electrodes which do not deteriorate with high currents and 3) better focusing of the potential on and after a few hundred microns.

Another characteristic of the invention concerns the surface conductivity of the interface between the ground grid or more generally the surface 3 and the electrolyte, it being specified that it is not the conductivity of the metal forming the ground grid that is taken into account, but rather the conductivity of the metal/physiological solution or metal/tissue electrochemical interface. The surface conductivities are considered for signal frequencies of between 10 and 100,000 Hz and notably from 100 Hz to 1,000 Hz, the standard frequency being 1,000 Hz. FIG. 13 shows the progression of potential V in relation to the distance x along the abscissa from a stimulating microelectrode positioned at x=0 microns for different surface conductivities of the ground grid: 40 S/m² (curve C51), 400 S/m² (curve C52), 4,000 S/m² (curve C53), 40,000 S/m² (curve C54), infinite conductivity (curve C55). The greater the surface conductivity of the ground grid, the more the stimulation is focussed. In practice, values of >1,000 S/m² can be used, which are higher than those of platinum electrodes and which can be obtained for example with other materials or with rough, porous or functionalized surfaces (for example black platinum). It is to be understood that the type of conductivity considered here is the conductivity per unit of geometric surface and not of real surface. A rough or porous interface will effectively have a real (deployed/developed) area that is greater than a same smooth geometric surface. Values of conductivity in the order of 400

S/m² are obtained by conductive parts in crude white platinum for example. Conductivity values in the order of 40,000 S/m² are obtained for example with conductive parts in black treated platinum.

LIST OF CITED REFERENCES

[1] Microelectrode arrays for stimulation of neural slice preparations: D. A. Borkholder, J. Bao, N. I. Maluf, E. R. Perl, G. T. A. Kovacs, Journal of Neuroscience Methods 77 (1997) 61-66.
[2] Fabrication of microelectrode arrays for neural measurements from retinal tissue: W. Cunningham, K. Mathieson, F. A. McEwan, A. Blue, R. McGeachy, J. A. McLeod, C. Morris-Ellis, V. O'Shea, K. M. Smith, A. Litke, M. Rahman, Journal of Physics D: Applied Physics 34 (2001) 2804-2809.
[3] Sheet conductor model of brain slices for stimulation and recording with planar electronic contacts: P. Fromherz, Eur Biophys J (2002) 31:228-231.
[4] Effective parameters for stimulation of dissociated cultures using multi-electrode arrays: Daniel A. Wagenaar, Jerome Pine, Steve M. Potter, Journal of Neuroscience Methods 138 (2004) 27-37.
[5] Multi-electrode stimulation and recording in the isolated retina: Andrew E. Grumet, John L. Wyatt, Joseph F. Rizzo, Journal of Neuroscience Methods 101 (2000) 31-42.
[6] A three-dimensional multi-electrode array for multi-site stimulation and recording in acute brain slices: Marc Olivier Heuschkel, Michael Fejtl, Mario Raggenbass, Daniel Bertrand, Philippe Renaud, Journal of Neuroscience Methods 114 (2002) 135-148.
[7] U.S. Pat. No. 5,411,540.
[8] PCT Patent application No. WO 2005/087309.

The invention claimed is:

1. A device to stimulate a living tissue, the device comprising:
an array of microelectrodes arranged in a determined configuration side-by-side, each microelectrode comprising a section for local application to the living tissue and a conductor for sending a stimulation signal, wherein each microelectrode can be selected for application of an electric stimulation signal;
the microelectrodes being insulated from each other;
the conductors for sending a stimulation signal being insulated from each other;
the local application sections being insulated from each other;
a plurality of conductive zones being located, respectively for a determined plurality of microelectrodes, in the vicinity of the plurality of local application sections of the determined microelectrodes of the array and being insulated from these local application sections;
the plurality of conductive zones belonging to a conductive surface supplemental to the microelectrodes and separate from the microelectrodes, the supplemental conductive surface being used for all or part of the application against the living tissue;
at least one connector causing electric connection between the plurality of conductive zones of the supplemental surface for all the determined plurality of microelectrodes insulated from one another, so that the conductive zones of the supplemental surface are substantially equipotential; and
the supplemental conductive surface also being connected to at least one port intended to be connected to an external return conductor returning at least part of the stimulation signal and being formed to ensure focal stimulation from at least one of the determined plurality of microelectrodes and to act as a common focus for several application sections of different determined microelectrodes.

2. The device according to claim 1, further comprising a single supplemental conductive surface.

3. The device according to claim 1, wherein the number of supplemental surfaces is less than one tenth of the number of microelectrodes in the array.

4. The device according to claim 1, wherein there are several supplemental surfaces that are substantially equipotential.

5. The device according to claim 1, wherein there are several supplemental surfaces at substantially different potentials.

6. The device according to claim 1, wherein the potential of the at least one supplemental surface is different from the potential of at least one microelectrode of the determined plurality of microelectrodes.

7. The device according to claim 1, wherein the supplemental conductive surface is integrated in the same support as that of the microelectrodes.

8. The device according to claim 1, wherein the supplemental conductive surface is integrated on a different support to the support of the microelectrodes.

9. The device according to claim 1, wherein the supplemental conductive surface is in the form of a grid whose conductive zones are formed by meshes passing around microelectrodes, the connector being formed on the supplemental surface by the intersections of the meshes with each other.

10. The device according to claim 9, wherein the meshes passing around microelectrodes each surround a single microelectrode.

11. The device according to claim 9, wherein the grid is formed by rectilinear secant lines.

12. The device according to claim 9, wherein each of the meshes of the grid surrounding a microelectrode form a stimulation pixel restricted to the space delimited by this mesh.

13. The device according to claim 1, wherein the supplemental conductive surface passes between microelectrodes.

14. The device according to claim 1, wherein the supplemental conductive surface surrounds microelectrodes.

15. The device according to claim 1, wherein the supplemental conductive surface is continuous with openings for passing of the local application sections of microelectrodes.

16. The device according to claim 1, wherein the supplemental conductive surface comprises branches electrically parallel between microelectrodes and each passing in the vicinity of several microelectrodes.

17. The device according to claim 1, wherein the at least one electric connector between the different conductive zones is located at least partly in the supplemental conductive surface.

18. The device according to claim 1, wherein the at least one electric connector is located at least partly outside the supplemental conductive surface, inside or outside a support of the supplemental conductive surface or in an supplemental external electric circuit.

19. The device according to claim 1, wherein the supplemental conductive surface has an interface surface electric conductivity with the living tissue of 100 S/m² or higher, at a frequency of 100 Hz to 1,000 Hz.

20. The device according to claim 1, wherein the supplemental conductive surface has an interface surface electric conductivity with the living tissue of 1,000 S/m² or higher at a frequency of 100 Hz to 1,000 Hz.

21. The device according to claim 1, wherein the array of microelectrodes has a pitch distance between microelectrodes, and the conductive zones of the supplemental surface pass at a distance from the plurality of microelectrodes that is equal to or less than five times the maximum pitch distance between microelectrodes.

22. The device according to claim 1, wherein the conductive zones of the supplemental surface pass at a distance from the plurality of microelectrodes equal to or less than 500μm.

23. The device according to claim 1, further comprising a multiplicity of electric ports for access to the microelectrodes which are respectively associated with the multiplicity of microelectrodes of the array, the port of the supplemental conductive surface being single and separate from the electric ports of the microelectrodes.

24. The device according to claim 1, further comprising a multiplicity of electric ports for access to the microelectrodes which are respectively associated with the multiplicity of microelectrodes of the array, the port of the supplemental conductive surface being multiple and separate from the electric ports of the microelectrodes.

25. The device according to claim 1, wherein the microelectrodes located on the edge of the array delimit a region for application against the living tissue, and the port of surface is positioned outside the application region of the microelectrodes.

26. The device according to claim 1, wherein the microelectrodes located on the edge of the array delimit a region for application against the living tissue, and the port of the surface is positioned inside the application region of the microelectrodes.

27. The device according to claim 1, further comprising a first system operably generating electric stimuli and amplifying and multiplexing of signals recorded with the microelectrodes, connected to the microelectrodes and to the port of the surface, a second system operably acquiring and controlling a man-machine interface to control the first system so as to send to at least one preselected microelectrode a stimulation signal pre-determined on the man-machine interface and so as to collect the response of the living tissue to the stimulation signal and to reproduce it on the man-machine interface.

28. The device according to claim 1 wherein the microelectrodes contact a cell preparation, an explant, a living organism, a laboratory system, an isolated living organ, and a part of an isolated living organ in vitro.

29. The device according to claim 1, including A removable assembly intended to be mounted in the device according to claim 1, further comprising, on one same removable module or distributed over several separate removable modules, it comprises the array of microelectrodes, said supplemental surface, an input-output electric interface circuit for electric connection of the microelectrodes and of the supplemental surface with the outside, comprising a multiplicity of electric terminals for access to respectively the multiplicity of microelectrodes of the array and a terminal of the supplemental surface separate from the electric terminals of the microelectrodes.

30. The device according to claim 1 wherein the microelectrodes record signals emitted by a living tissue.

* * * * *